US006878377B2

(12) United States Patent
Rook et al.

(10) Patent No.: US 6,878,377 B2
(45) Date of Patent: Apr. 12, 2005

(54) MYCOBACTERIUM VACCAE FOR DOWN-REGULATION OF THE TH2 ACTIVITY OF THE IMMUNE SYSTEM

(75) Inventors: Graham A. Rook, London (GB); John L. Stanford, London (GB); Alimuddin L. Zumla, London (GB)

(73) Assignee: Stanford Rook Limited, London (GB)

(*) Notice: Subject to any disclaimer, the term of this patent is extended or adjusted under 35 U.S.C. 154(b) by 2 days.

(21) Appl. No.: 09/761,762

(22) Filed: Jan. 18, 2001

(65) Prior Publication Data

US 2001/0018057 A1 Aug. 30, 2001

Related U.S. Application Data

(63) Continuation of application No. 09/319,368, filed as application No. PCT/GB97/03460 on Dec. 17, 1997, now abandoned.

(30) Foreign Application Priority Data

Dec. 18, 1996 (GB) ............................................. 9626215
Dec. 24, 1996 (GB) ............................................. 9626859

(51) Int. Cl.$^7$ ........................ A61K 39/04; A61K 39/38; A61K 39/02; C12N 1/00; C12N 1/12

(52) U.S. Cl. .................... 424/248.1; 424/9.2; 424/93.1; 424/184.1; 424/234.1; 424/278.1; 435/41; 435/243; 435/253.1; 435/863

(58) Field of Search ............................. 424/9.2, 184.1, 424/234.1, 248.1, 278.1, 93.1; 435/41, 243, 253.1, 863

(56) References Cited

U.S. PATENT DOCUMENTS 4,724,144 A    2/1988    Rook et al.

FOREIGN PATENT DOCUMENTS

| WO | WO 85 05034 A | 11/1985 |
|----|---------------|---------|
| WO | WO 91 02542 A | 3/1991  |
| WO | WO 92 08488 A | 5/1992  |
| WO | WO 93 16727 A | 9/1993  |
| WO | WO 94 06466 A | 3/1994  |
| WO | WO 95 26742 A | 10/1995 |
| WO | WO 96 11014 A | 4/1996  |

OTHER PUBLICATIONS

Evans, "Chronic Fatigue Syndrome: thoughts on pathogenesis", Reviews of Infectious Diseases 13(suppl. 1):S56–S59 (1991).
Sharfran et al, "The Chronic Fatigue Syndrome ", The American Journal of Medicine 90:730–739 (1991).
Herberman, "Sources of Confounding in Immunologic Data", Reviews of Infectious Diseases 13(suppl. 1):S84–S86 (1991).

Shulte, "Validation of biologic markers for use in research on Chronic Fatigue Syndrome", Reviews of Infectious Diseases 13(suppl. 1):S87–S89 (1991).
Holmes, "Defining the Chronic Fatigue Syndrome", Reviews of Infectious Diseases 13(suppl. 1):S53–S55 (1991).
Holmes, "Chronic Fatigue Syndrome: A working case definition", Annals of Internal Medicine 108:387–389 (1991).
Grange et al, "Role of viral infections in the inception of childhood asthma and allergies", Thorax 50:701 (1994).
Seah and Rook, "A sensitive, non–radioactive quantitative method for measuring IL–4 and IL4$\delta$2 mRNA in unstimulated cells from multiple clinical samples, using nested RT–PCR", Journal of Immunological Methods 228:139–149 (1999).
Seah et al, "Type 2 Cytokine Gene Activation and Its Relationship to Extent of Disease in Patients with Tuberculosis", The Journal of Infectious Diseases 181:385–389 (2000).
Yang et al, "Murine studies using polyethylene glycol–modified recombinant human interleukin 2 (PEAG–IL–2): antitumor effects of PEG–alone and in combination with adoptive cellular transfer", Lymphokine Cytokine Res. 10(6):475–480 (1991)—Abstract.
Cameron et al, "Synergistic antitumor activity of tumor–infiltrating lymphocytes interleukin 2, and local tumor irradiation. Studies on the mechanism of action", J. Exp. Med. 171(1):249–263 (1990)—Abstract.
Cameron et al, "Synergistic antitumor effects of combination immunotherapy recombinant interleukin–2 and a recombinant hybrid alpha interferon in the treatment of established murine hepatic metastases", Cancer Res. 48(20):5810–5817 (1988)—Abstract.
Papa et al, "Combined effects of chemotherapy and interleukin 2 in the therapy of mice with advanced pulmonary tumors", Cancer Res. 48(1):122–129 (1988)—Abstract.
Lotze et al, "In vivo administration of purified human interleukin–2 to patients with cancer: development of interleukin–2 receptor positive cells and circulating soluble interleukin–2 receptors following interleukin–2 administration", Cancer Res. 47(8):2188–2195 (1987)—Abstract.
Schwartzentruber, "Guidelines for the safe administration of high–dose interleukin–2", J. Immunother. 24(4):287–293 (2001)—Absract.

(Continued)

Primary Examiner—Rodney P Swartz
(74) Attorney, Agent, or Firm—Nixon & Vanderhye PC

(57) ABSTRACT

Antigenic and/or immunogenic material derived from *Mycobacterium vaccae* is used to down-regulate Th2 activity of the immune system without up-regulation of Th1 activity. Disorders such as Chronic Fatigue Syndrome, Gulf War Syndrome and Total Allergy Syndrome are treated. The material preferably comprises dead *M. vaccae* cells in a composition which does not include a non-*M. vaccae* antigen, immunogen or allergen.

4 Claims, 10 Drawing Sheets

OTHER PUBLICATIONS

Figure 1:
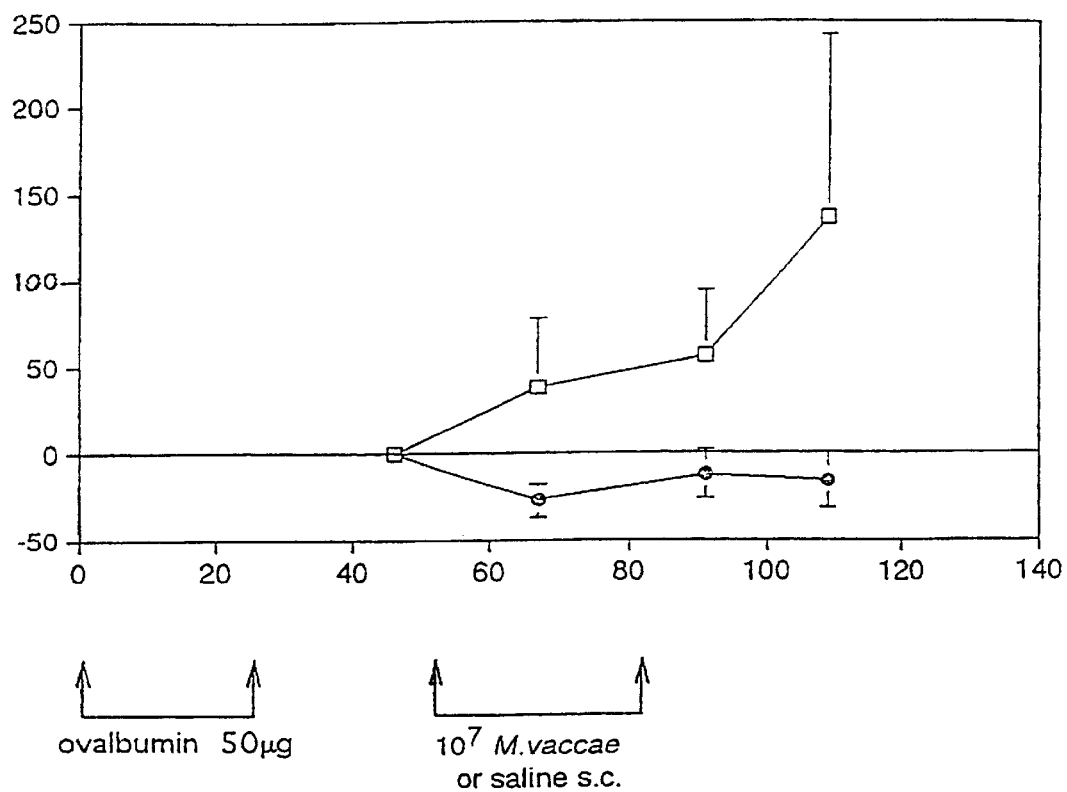

Scott et al, "Treatment of active rheumatoid arthritis with leflunomide: two year follow up of a double blind, placebo controlled trial versus sulfasalazine", Ann. Rheum. Dis. 60(10):913–923 (2001)—Abstract.

Kalden et al, "Improved functional ability in patients with rheumatoid arthrtis–longterm treatment with leflunomide versus sulfasalazine", J. Rheumatol 28(9):1983–1991 (2001)—Abstract.

Burkhardt and Kalden, "Xenobiotic immunosuppressive agents: therapeutic effects in animal models of autoimmune diseases", Rheumatol. Int. 17(3):85–90 (1997)—Abstract.

Guo et al, "Immunosuppression preventing concordant xenogeneic islet rejection is not sufficient to prevent recurrence of autoimmune diabetes in nonobese diabetic mice", Transplantation 65(10):1310–1314 (1998)—Abstract.

Xu et al, "In vivo mechanism by which leflunomide controls lymphoproliferative and autoimmune disease in MRL/MpJ. lpr/lpr mice", J. Immunol. 159(1):167–174 (1997)—Abstract.

Jarman et al, "Inhibition of murine lgE and immediate cutaneous hypersensitivity responses to ovalbumin by the immunomodulatory agent leflunomide", Clin. Exp. Immunol. 115(2):221–228 (1999)—Abstract.

Stosic–Grujicic et al, "Leflunomide protects mice from multiple low dose streptozotocin (MLD–SZ)–induced insulitis and diabetes", Clin. Exp. Immunol. 117(1):44–50 (1999)—Abstract.

Borish et al, "Chronic fatigue syndrome: Identification of distinct subgroups on the basis of allergy and psychologic variables", J. Allergy Clin. Immunol. 102(2):222–230 (1998).

Straus et al, "Allergy and the chronic fatigue syndrome", Allergy Clin. Immunol. 81(5), Part 1:791–795 (1988).

Chao et al, "Altered Cytokine Release In Peripheral Blood Mononuclear Cell Cultures From Patients With The Chronic Fatigue Syndrome", Cytokine 3(4):292–298 (1991).

Bennett et al, "Elevation of Bioactive Transforming Growth Factor–β in Serum from Patients with Chronic Fatigue Syndrome", Journal of Clinical Immunology 17(2):160–166 (1997).

Visser et al, "CD4 T Lymphocytes from Patients with Chronic Fatigue Syndrome Have Decreased Interferon–γ Production and Increased Sensitivity to Dexamethasone", The Journal of Infectious Diseases 177:451–454 (1998).

Conti et al, "Eosinophil cationic protein serum levels and allery in chronic fatigue syndrome", Allergy 51:124–127 (1996).

Wang & Rook, "Inhibition of an established allergic response to ovalbumin in BALB/c mice by killed *Mycobacterium vaccace*", Immunology 93:307–313 (1998).

Tükenmez et al, "Effect of pre–immunization by killed *Mycobacterium bovis* and *vaccae* on immunoglobulin E response in ovalbumin–sensitized newborn mice", Pediatric Allergy Immunol. 10:107–111 (1999).

Cottrez et al, "T Regulatory Cells 1 Inhibit a Th2–Specific Response In Vivo", The Journal of Immunology 165:4848–4853 (2000).

Zuany–Amorim et al, "Suppression of airway eosinophilia by killed *Mycobacterium vaccae*–induced allergen–specific regulatory T–cells", Nature Medicine 8(6):625–629 (2002).

Arkwright et al, "Intradermal administration of a killed *Mycobacterium vaccae* suspension (SRL 172) is associated with improvement in atopic dermatitis in children with moderate–to–severe disease", J. Allergy Clin. Immunol 107:531–534 (2001).

Breivik & Rook, "Prevaccination with SRL 172 (heat–killed Mycobacterium vaccae) inhibits experimental periodontal disease in Wistar rats", Clin. Exp. Immunol. 120:463–467 (2000).

Rook and Zumla, "Gulf Ware syndrome: is it due to a systemic shift in cytokine balance towards a Th2 profile?", 349:1831–1833 (1997).

Wallace et al, "A type 2 (Th2–like) pattern of immune response predominates in the pulmonary interstitium of patients with cryptogenic fibrosing alveolitis (CFA)", Clin. Exp. Immunol. 101:436–441 (1995).

Wynn et al, "An IL–12 based vaccination method for preventing fibrosis induced by schistosome infection", Nature 376:594–597 (1995).

Lawrence et al, "IL–4–regulated enteropathy in an intestinal nematode infection", Eur. J. Immonol. 28:2672–2684 (1998).

Seah and Rook, "IL–4 Influences Apoptosis of Mycobacterium–Reactive Lymphocytes in the Prsence of TNF–α", The Journal of Immunology 167:1230–1237 (2001).

Lee et al, "Interleukin–13 Induces Tissue Fibrosis by Selectively Stimulating and Activating Transforming Growth Factor $\beta_1$", J. Exp. Med. 194(6):809–821 (2001).

Atamas et al, "Production of Type 2 Cytokines By CD8+ Lung Cells is Associated With Greater Decline in Pulmonary Function in Patients With Systemic Sclerosis", Arthritis & Rheumatism 42(6):1168–1178 (1999).

Seah and Rook, "High Levels of mRNA Encoding IL–4 in Unstimulated Peripheral Blood Mononuclear Cells from Tuberculosis Patients Revealed by Quantitative Nested Reverse Transcriptase–Polymerase Chain Reaction; Correlations with Serum IgE Levels", Scand. J. Infect. Dis. 33:106–109 (2001).

Tsunoda et al, "Enhancement of Experimental Allergic Encephalomyelitis (EAE) by DNA Immunization with Myelin Proteolipid Protein (PLP) Plasmid DNA", Journal of Neuropathology and Experimental Neurology 57(8):758–767 (1998).

A.

B.

C.

A.

B.

MYCOBACTERIUM VACCAE FOR DOWN-REGULATION OF THE TH2 ACTIVITY OF THE IMMUNE SYSTEM

This is a continuation of application Ser. No. 09/319,368, filed Jun. 4, 1999, now pending, which is a 371 of PCT/GB97/03460, filed Dec. 17, 1997 the entire content of which is hereby incorporated by reference in this application.

The present invention relates to treatment of disorders which are characterised by a shift in activity of the immune system from Th1 activity to Th2 activity. It is founded on the surprising discovery that preparations of *Mycobacterium vaccae* are able to effect a non-specific systemic Th1 bias, in particular by down-regulation of Th2 activity without concomitant up-regulation of Th1 activity. Disorders to which the present invention may be applied include Chronic Fatigue Syndrome, Gulf War Syndrome and Total Allergy Syndrome.

Patients with Chronic Fatigue Syndrome (CFS) (Turnberg et al.) may have a higher incidence of allergic phenomena, twice the number of allergic skin reactions, and low activity of NK cell activity and low production IFNγ and IL-2 (Straus, 1996). Some have high levels of antibody to EB virus, which is also a feature of individuals with a decreased Th1 activity. They also have mood changes and depression. These features are all compatible with a Th1 to Th2 switch in cytokine profile. This bias may be a consequence of the modern life-style, which fails to expose the population to sufficient Th1-inducing stimuli, and rather tends to expose it to Th2-inducing immunisations and allergens.

The present inventors believe that Gulf War Syndrome represents a special case of CFS, where the Th2-inducing stimuli can be identified, because Gulf War personnel were given multiple Th-2-inducing vaccinations. Vaccinations or infections can exert a systemic effect, and non-specifically increase or reduce the Th1/Th2 cytokine balance of the response to other unrelated antigens (Shaheen et al., 1996, Shirakawa et al., 1996), and affect (positively or negatively) survival from unrelated diseases (Aaby, 1996, Aaby et al., 1995). The inventor' belief that these vaccinations used in the Gulf induced a systemic Th2 switch is supported by four features of the vaccination protocol:

(i) Pertussis was used as an adjuvant in British troops in the Gulf and its adjuvanticity is potently Th2 (Mu & Sewell, 1993, Ramiya et al., 1996, Smit et al., 1996).

(ii) Gulf War troops were given Th2-inducing immunogens, against plague, anthrax, typhoid, tetanus and cholera. Furthermore, such a large antigen load tends to drive the response towards Th2 (Aaby, 1995, Bretscher et al., 1992, Hernandez-Pando & Rook, 1994).

(iii) The vaccinations were given after deployment of the troops in the war zone, or just before they travelled there, at a time when stress levels will have been high. Immunisation in the presence of raised levels of glucocorticoids (i.e. cortisol) drives the response towards Th2 (Bernton et al., 1995, Brinkmann & Kristofic, 1995, Ramirez et al., 1996).

(iv) The troops were also exposed to carbamate and organophosphorous insecticides, and these inhibit IL-2-driven phenomena essential for normal Th1 function (Casale et al., 1993). The importance of this component is uncertain. However, it has been rumoured that the insecticides were often obtained from local sources in the Gulf, so purity was not known, and even more toxic contaminants may have been present.

Thus, multiple vaccinations administered under these circumstances may have caused a long-lasting systemic cytokine imbalance. The same effect will occur sporadically in the general population, due to vaccinations or other Th2-inducing environmental stimuli and infections, and can account for the widespread incidence of Chronic Fatigue Syndrome.

These points are explained in greater detail below.

The present inventors have made the surprising observation that preparations of (killed) *Mycobacterium vaccae* are potently able to redress in a non-specific manner a systemic Th1→Th2 bias. The effect is to bias immune system activity away from Th2 in a way that encompasses the immune response to antigens that are not present within the *M. vaccae* preparation injected.

This has been demonstrated experimentally both in an animal model and in man. Representative experiments are described in detail below. In particular, they surprisingly show a down-regulation of Th2 activity, which may not be coupled with up-regulation of Th1 activity.

Briefly, in experimental animals a non-specific systemic bias away from Th2 activity on administration of *M. vaccae* can be seen as a reduction in the titre of an IL-4 (Th2) dependent antibody response to ovalbumin (an allergen unrelated to *M. vaccae* itself), in mice pre-immunised so as to establish a Th2 response. A single injection of *M. vaccae* is able to cause this effect, and further injections can enhance it. The effect is non-specific because it does not require the presence of any component of ovalbumin in the injected preparation.

In humans (cancer patients) the effect has been demonstrated by the appearance in the peripheral blood of lymphocytes that spontaneously secrete IL-2 (a characteristic Th1 cytokine) and a decrease in T cells that secrete IL-4 (a characteristic Th2 cytokine) after stimulation with phorbol myrystate acetate and calcium ionophore. The percentage of lymphocytes showing this activated Th1 phenotype increases progressively after each successive injection of *M. vaccae*, reaching a plateau in many individuals after 3–5 injections of $10^9$ organisms (days 0, 15, 30 and then monthly).

Moreover, reports are included below of human subjects suffering from Chronic Fatigue Syndrome to whom *M. vaccae* preparations have been administered with beneficial effects.

*M. vaccae* has previously been disclosed by the present inventors for use in treatment of tuberculosis (GB-A-2156673), cancer (ZA 95/2644), HIV (WO94/06466) and chronic inflammation (GB-B-2252044). WO92/08488 (also from the present inventors) discloses its use as an adjuvant for administration with an antigen of interest, noting a conversion of the T-cell component of the response to the antigen from the Th2 pattern to the Th1 pattern. There is not in WO92/08488 any suggestion that *M. vaccae* can cause a non-specific Th2/Th1 shift in the activity of the immune system, that is any shift other than in the response specifically mounted to the antigen administered with the *M. vaccae*. Furthermore there is neither in WO92/08488 nor elsewhere any suggestion that it can down-regulate Th2 activity without concomitantly up-regulating Th1 activity.

Reviews of *M. vaccae* as a Th1 adjuvant include Abou-Zeid et al. (1997), Skinner et al. (1997a), and Skinner et al. (1997b). See also Mosmann and Sad (1996) which reviews up-regulation of Th1 cytokine having an inhibitory effect on Th2 cell proliferation.

The present invention generally relates to down-regulation of Th2 activity of the immune system of an individual without up-regulation of Th1 activity, particularly in treatment of a disorder characterised by a shift in immune system activity from Th1 to Th2 activity, in particular where down-regulation of Th2 activity is beneficial without concomitant up-regulation of Th1 activity.

In one aspect the present invention provides a method of treatment of an individual, the method including administration to the individual of antigenic and/or immunoregulatory material of *Mycobacterium vaccae.*

A further aspect of the present invention provides use of antigenic and/or immunoregulatory material of *Mycobacterium vaccae* in the manufacture of a medicament for treatment of an individual.

Another aspect of the present invention provides a substance or composition for use in treatment of an individual, the substance or composition including antigenic and/or immunoregulatory material of *Mycobacterium vaccae.*

Preferably, the *M. vaccae* preparation is provided without any extraneous ("foreign") antigen, immunogen or allergen being included.

Disorders to be treated may be characterised by a general, non-specific bias of the patient's immune system from Th1 activity to Th2 activity. This may be assessed or diagnosed with reference to decreased IL-2 production or increased IL-4 or IL-5 production in the individual, or by detection of IL-13, as a representative of the Th2 cytokines, and interferon gamma (IFNγ) as a representative Th1 cytokine. Other Th1/Th2 cytokines may be considered. A non-specific shift from Th1 to Th2 activity of the immune system may be not attributed to or caused by exposure of the individual to a particular antigen, or infection by a particular pathogen. Individuals to be treated may be not suffering from tuberculosis or other mycobacterial infection. Particular disorders that may be treated in accordance with the present invention include Chronic Fatigue Syndrome, Gulf War Syndrome and Total Allergy Syndrome (Straus, 1996). Other disorders in which a down-regulation of Th2 activity without up-regulation of Th1 is beneficial may be treated in accordance with the present invention.

Chronic Fatigue Syndrome may be operationally defined, for instance using the so-called 1994 CDC criteria (Fukuda et al.) or the so-called Oxford criteria (Sharpe et al.). Current knowledge about Chronic Fatigue Syndrome is summarised and discussed in Turnberg et al. (published October 1996).

The *Mycobacterium vaccae* material may be or include dead cells of *M. vaccae*. Such cells may be killed, for instance using irradiation, e.g. from $^{60}$Cobalt at a dose of 2.5 megarads, chemically, or by any other means, although autoclaving is preferred, e.g. at 69 kPa for 10 minutes at 115° C.–125° C. Autoclaving may yield a more effective preparation than irradiation.

Prior to being killed, *M. vaccae* cells may be grown on a suitable solid medium. A modified Sauton's liquid medium may be preferred (Boyden et al.), solidified with agar, preferably 1.3% agar. After aerobic incubation, generally at 32° C. for 10 days, the organisms may be harvested, then weighed and suspended in diluent, ready for administration. Storage, if required before use, may be at 4° C.

Instead of growing the cells on a solid medium, a liquid medium, such as the modified Sauton's medium (Boyden et al.), may be employed, for instance in a fermentor.

The diluent may be unbuffered saline, pyrogen-free. Preferably, the diluent is borate-buffered, preferably containing a surfactant such as Tween 80®. A suitable borate buffer is: $Na_2B_4O_7.10H_2O$-3.63 g, $H_3BO_3$-5.25 g, NaCl-6.19 g, Tween 80® 0.0005%, distilled water to 1 liter. These diluents are pharmaceutically acceptable.

The human results mentioned above have been obtained by administration of *M. vaccae* as the GMP preparation, SRL172, which is available for human use under several investigator IND's from the Federal Drug Administration, and CTX's from the Medicines Control Agency in the UK. GLP acute toxicology has been performed by Huntingdon Research. Phase 1 and Phase 2 safety data have been obtained in the USA, and lodged with the FDA. SRL172 is in Phase 3 trials for the immunotherapy of tuberculosis. SRL172 may be preferred for use in the present invention.

SRL172 is a *M. vaccae* formulation derived from the strain denoted R877R which was deposited under the Budapest Convention at the National Collection of Type Cultures (NCTC) Central Public Health Laboratory, Colindale Avenue, London NW9 5HT, United Kingdom, on Feb. 13, 1984 under the number NCTC 11659. R877R was originally isolated from mud samples from the Lango district of Central Uganda (Stanford and Paul).

Other *M. vaccae* strains may be used instead of SRL172. An organism can be identified as belonging to *M. vaccae* by biochemical and antigenic criteria (Bonicke et al.).

It is preferred for the present invention that the *M. vaccae* material is administered free or substantially free from non-*M. vaccae* antigenic or immunoregulatory material. In other words the medicament or composition to be administered may include, or may consist essentially of, *M. vaccae* antigenic and/or immunoregulatory material, such as dead cells, an extract or derivative thereof, and a pharmaceutically acceptable diluent.

Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage etc, is within the responsibility of general practioners and other medical doctors.

A single dosage (where dead cells are to be administered) will generally contain from $10^7$ to $10^{10}$ killed *M. vaccae* microorganisms. Patients may be administered a single dose of $10^8$ to $10^9$ killed *M. vaccae*, though the dose may be repeated if need be, for instance at intervals from 2 weeks to 6 months.

A composition may be administered alone or in combination with other treatments, either simultaneously or sequentially dependent upon the condition to be treated.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which is preferably by injection, e.g. cutaneous, subcutaneous or intra-dermal.

For injection, the active ingredient will be in the form of a parenterally acceptable aqueous solution which is pyrogen-free and has suitable pH, isotonicity and stability. Suitable diluents, which are pharmaceutically acceptable and may be preferred, have been discussed already above.

Oral administration may be used, in which case the pharmaceutical composition may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

M. vaccae may be administered by aerosol to the airways, using a suitable formulation, e.g. including particles of a size which travels to the appropriate parts of the airways. This may be a dried powder rather than aqueous suspension.

Instead of killed cells, material derived from M. vaccae may be used, in particular an extract or a synthetic molecule which has the requisite activity.

As has been discussed briefly already above, multiple vaccinations, stress and other factors may have caused a long-lasting systemic cytokine imbalance in Gulf War veterans. The same effect will occur sporadically in the general population, due to vaccinations or other Th2-inducing environmental stimuli and infections, and can account for the widespread incidence of Chronic Fatigue Syndrome.

Potent immunogens can have systemic long-lasting non-specific effects on the nature of the immune response to unrelated antigens. For instance measles infection reduces the incidence of atopy, and of allergic reactions to House Dust Mite (Shaheen et al., 1996). Similarly, Japanese children that are tuberculin skin-test positive are less likely to be atopic than are tuberculin negative children, and their ratio of circulating Th1/Th2 cytokines is higher. Moreover after repeated injection of BCG, those in whom tuberculin conversion occurs have an increased probability of losing their atopic symptoms in (Shirakawa et al., 1996).

Measles vaccination is another example. This vaccine, when used at the standard dose, reduced mortality by considerably more than can be accounted for by the incidence of measles in the unvaccinated population. Diphtheria, tetanus and pertussis vaccines (Th2-inducing) do not show this non-specific protective effect (Aaby et al., 1995). However when a high titre measles vaccine was used the mortality increased, though protection from measles itself was maintained (Aaby, 1995, Aaby et al., 1995). There is evidence that this increase in mortality was accompanied by a switch towards Th2, and dose-related increases in the induction of a Th2 component are well established for several other immunogens (Bretscher et al., 1992, Hernandez-Pando & Rook, 1994). The vaccines used in the Gulf were Th2-inducing (plague, anthrax, typhoid, tetanus, cholera), and accumulatively constituted a large antigenic load, further favouring Th2. Moreover this tendency will have been increased by the use of pertussis as an adjuvant since it is a potent inducer of Th2 (Mu & Sewell, 1993, Ramiya et al., 1996, Smit et al., 1996). This property of pertussis has led recently to discussion of the possibility that its use in children contributes to the contemporary increased prevalence of atopy (Nilsson et al., 1996, Odent et al., 1994).

The innate tendency for these vaccines to drive a systemic Th2 response will have been greatly enhanced by endocrine factors secondary to the stress to which the Gulf War personnel were exposed at the time of vaccination.

Several steroid hormones modulate T cell responses. Dehydroepiandrosterone (DHEA) or unknown metabolites of DHEA, tend to promote a Th1 pattern. Thus DHEA can restore immune functions in aged mice, and correct dysregulated cytokine release seen in old animals (Daynes et al., 1993, Garg & Bondada, 1993). It has been tested for similar properties in aged humans (Morales et al., 1994). It enhances production of Th1 cytokines such as IL-2 and IFNγ (Daynes & Araneo, 1989, Daynes et al., 1990, Daynes et al., 1995, Daynes et al., 1991). DHEA also enhances IL-2 secretion from human peripheral blood T cells (Suzuki et al., 1991).

These effects of DHEA are the reverse of the effect of glucocorticoids such as cortisol which enhance Th2 activity and synergise with Th2 cytokines (Fischer & Konig, 1991, Guida et al., 1994, Padgett et al., 1995, Wu et al., 1991). If proliferation of "naive" T lymphocytes is driven in the presence of a non-specific stimulus (Brinkmann & Kristofic, 1995), or by an antigen (as follows vaccination) T lymphocytes with a Th2 cytokine profile will develop. This has been rather clearly shown with spleen cells from "clean" laboratory rodents which have few memory cells under normal circumstances (Ramirez et al., 1996).

Overall the "bottom line" is that cortisol favours the development of a Th2 cytokine profile from naive cells (Brinkmann & Kristofic, 1995). This point must not be confused with the fact that the cytokine-secreting activity of established Th2 cells is readily inhibited by cortisol. Thus the use of cortisol analogues for conventional treatments for Th-2-mediated diseases such as eczema, asthma and hay fever may work via anti-inflammatory effects, and by reducing cytokine production by Th2 cells (Corrigan et al., 1995), and yet at the same time the use of cortisol will encourage perpetuation of the underlying problem by driving newly recruited T cells towards Th2.

Psychological and physical stress activate the hypothalamo-pituitary-adrenal axis, and so lead to a variety of changes including increased production of cortisol. Excessive exercise and deprivation of food and sleep resulted in a falling ratio of DHEA to cortisol (DHEA/cortisol ratio). This correlated directly with a fall in delayed hypersensitivity (DTH) responsiveness (a Th1 marker), and there was a simultaneous rise in serum IgE levels. IgE is wholly dependent upon Th2 cytokine production (Bernton et al., 1995). This is to be expected in the light of the known effects of DHEA and cortisol outlined above.

A further example of the Th1→Th2 switching effect of stress is the increase in antibody to EB virus in students reacting in a stressed manner to their exams. This virus is usually controlled by a Th1 response and cytotoxic T cells, and loss of control results in virus replication and increased antibody (Zwilling, 1992). Similarly, peripheral blood leukocytes from medical students during exam periods showed lower mRNA for IFNγ, a Th1 cytokine (Glaser et al., 1993).

Similar points can be demonstrated in a more controlled manner in animals. Stress due to crowding or restraint can increase mycobacterial growth in tuberculous in mice (Brown et al., 1993, Tobach & Bloch, 1956). This is a model which is acutely sensitive to the presence of even a small Th2 component (Rook & Hernandez-Pando, 1996). Other examples have been discussed (Moynihan, 1994).

There is considerable evidence that depression can be associated with excessive cortisol-mediated effects in the brain (reviewed in (Raven et al., 1996)), and stress can lead to depression. Thus depression (as seen in CFS and GWS) tends to associate with Th2-mediated disorders, such as asthma, eczema, and some endocrine changes are common to Th2 disorders and to depression (Holsboer et al., 1984, Rupprecht et al., 1995).

In tuberculosis there is a systemic Th2 shift (Rook & Hernandez-Pando, 1996), and an unusual pattern of metabolites of adrenal steroids is excreted in the urine (Rook et al., 1996). Thus there are increased metabolites of cortisol relative to metabolites of cortisone. Treatment of the disease restores the Th1 dominance and corrects the pattern of steroid metabolites, so that metabolites of cortisone increase relative to metabolites of cortisol (Rook et al., 1996). Treatment of depression with the drug metyrapone causes the same change in steroid metabolites (e.g. increase in metabolites or cortisone relative to metabolites of cortisol) (Raven et al., 1995). The M. vaccae preparation SRL172 is effective in the immunotherapy of tuberculosis.

As discussed above, vaccinations can induce systemic non-specific changes in Th1/Th2 balance, as well as the antigen-specific immunisation that is usually sought. The treatment for CFS may require induction of a systemic non-specific Th1 bias in order to restore the dominance of Th1 over Th2 that is characteristic of normal healthy individuals. This is the opposite of the bias that may have been induced by the vaccinations received by personnel in the Gulf.

Experimental evidence provided herein now shows surprisingly that *Mycobacterium vaccae* preparations can reduce the detrimental Th1 to Th2 bias which may be seen in Gulf War veterans.

The present invention will now be illustrated without limitation with reference to experimental examples and the following figures:

FIG. 1 shows the change in total serum IgE (ng/ml±SD) in mice on various days following first immunisation with ovalbumin, calculated with respect to the value on day 46. The closed circles are for *M. vaccae* recipients; the open squares are for saline controls. For convenience, the days of immunisation with ovalbumin and administration of *M. vaccae* or saline are indicated.

Figure 2:
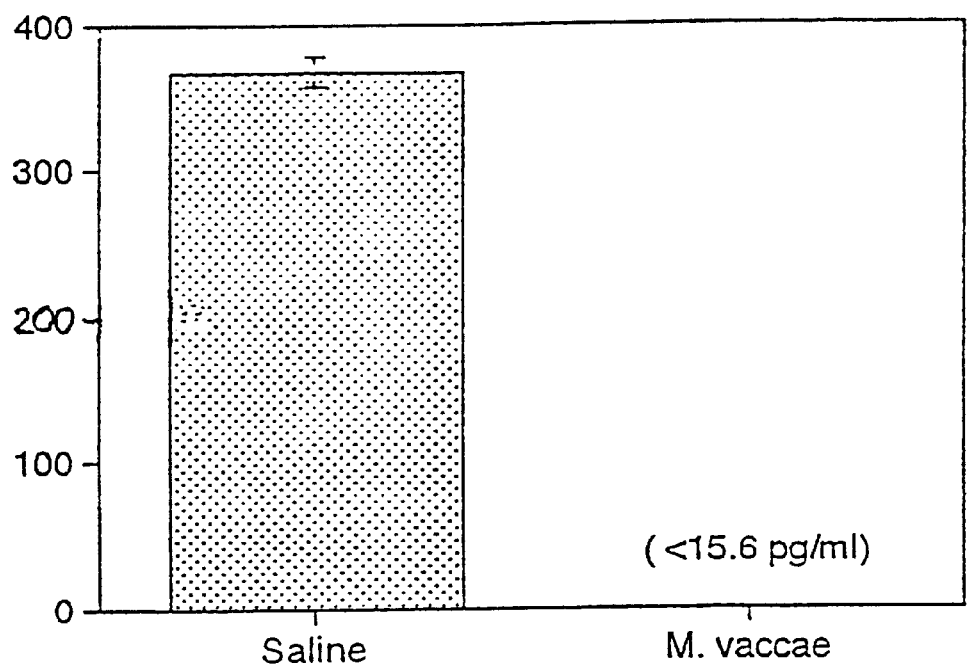

FIG. 2 shows measurements of IL-5 (pg/ml±SD) released in vitro from spleen cells taken from ovalbumin challenged mice. The minimum concentration detected by the assay used was 15.6 pg/ml.

Figure 3:
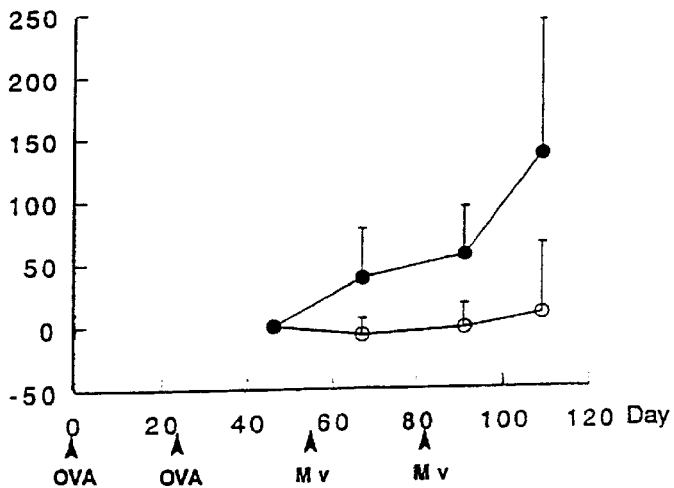
Figure 3:
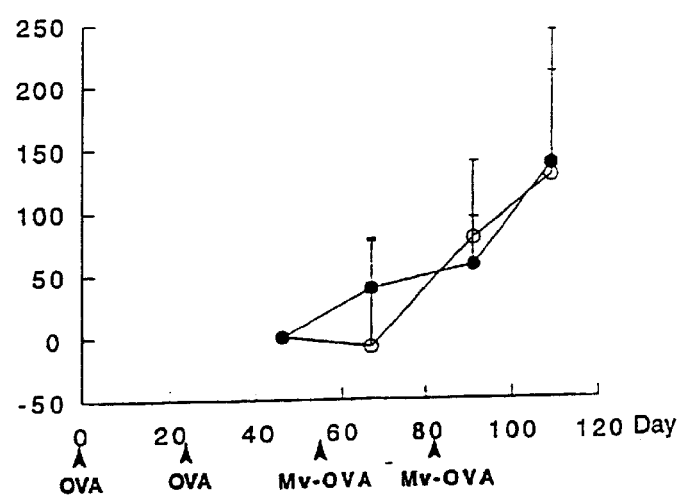
Figure 3:
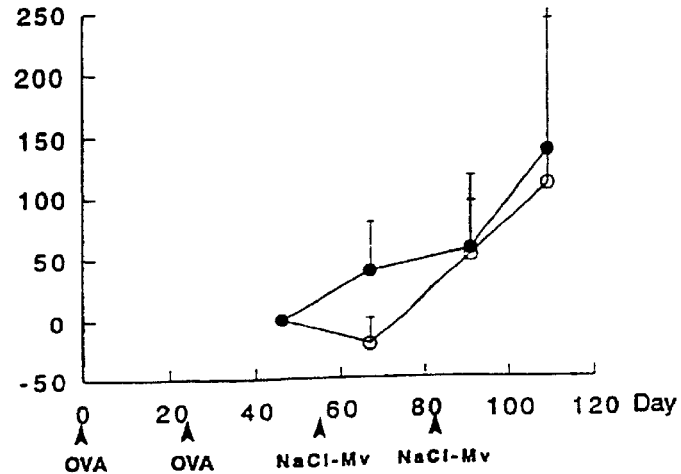

FIG. 3 shows the effect of treatment with s.c. injections of saline (•), compared to $10^7$ of the *M. vaccae* preparations (○), on total serum IgE (ng/ml), in BALB/c mice previously immunized with OVA. (FIG. 3A) $10^7$ unmodified *M. vaccae* (Mv), (FIG. 3B) OVA-conjugated *M. vaccae* (Mv-OVA), or (FIG. 3C) NaCl-washed and periodate-treated control *M. vaccae* (NaCl-Mv). Data are expressed as the change relative to readings obtained with the samples taken on day 46, ±SD. Immunization and treatment schedules are indicated on the Figs. (OVA:immunization with OVA 50 µg in IFA).

Figure 4:
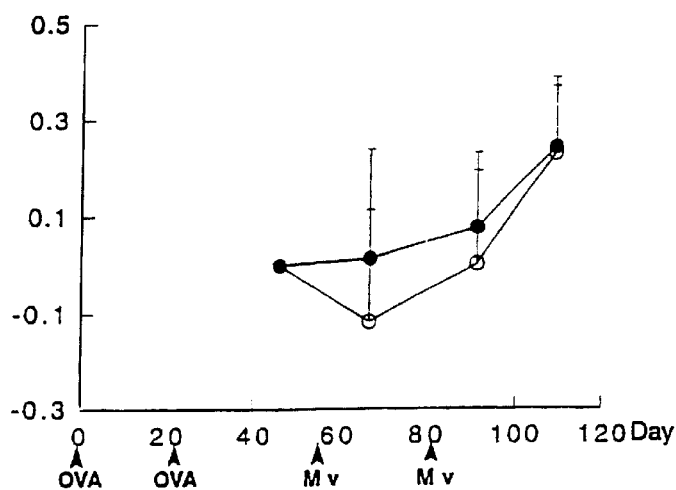
Figure 4:
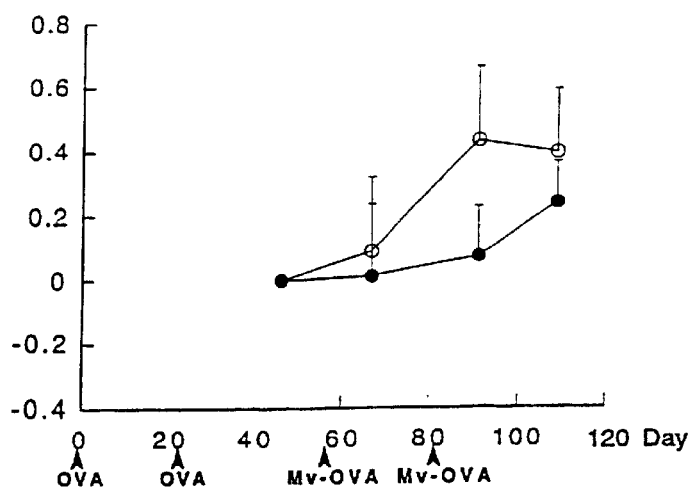
Figure 4:
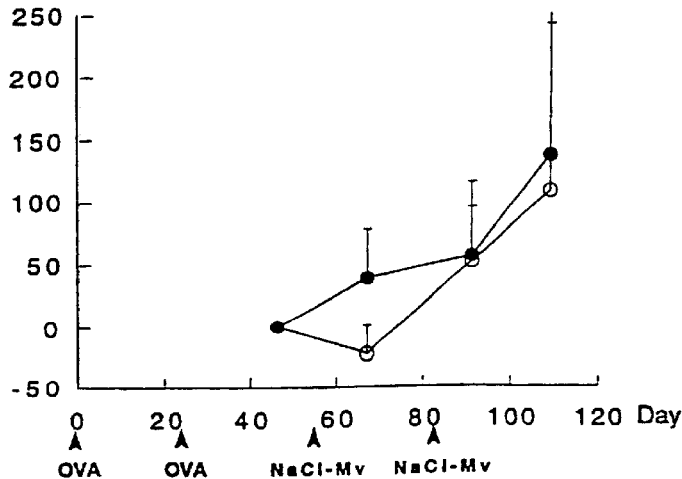

FIG. 4 shows the effect of treatment with s.c. injections of saline (•), compared to $10^7$ of the *M. vaccae* preparations (○), on OVA-specifc IgE, in BALB/c mice previously immunized with OVA. (FIG. 4A) unmodified *M. vaccae* (Mv) (O.D. 405 nm), (FIG. 4B) OVA-conjugated *M. vaccae* (MvOVA) (O.D. 405 nm), or (FIG. 4C) NaCl-washed and periodate-treated control *M. vaccae* (NaCl-Mv) (ng/ml). Data are expressed as the change relative to readings obtained with the samples taken on day 46, ±SD. Immunization and treatment schedules are indicated on the Figs.

Figure 5:
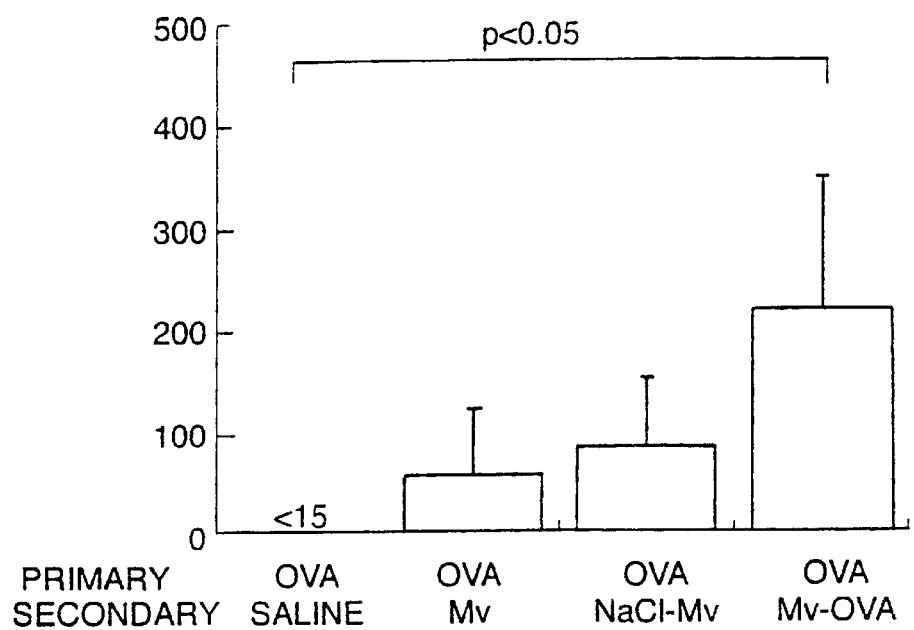

FIG. 5 shows production of IL-2 by splenocytes cultured with OVA. Spleens were obtained on day 109 from mice which had been immunised with OVA on days, 0 and 24, and treated on days 53 and 81 with saline, $10^7$ unmodified *M. vaccae* (Mv), OVA conjugated on *M. vaccae* (Mv-OVA), or the corresponding control NaCl-washed and periodate-treated control *M. vaccae* (NaCl-Mv). Culture supernatants were collected for IL-2 estimation after 24 hours. The data are presented as the mean levels of cytokine±SD (pg/ml.

Figure 6:
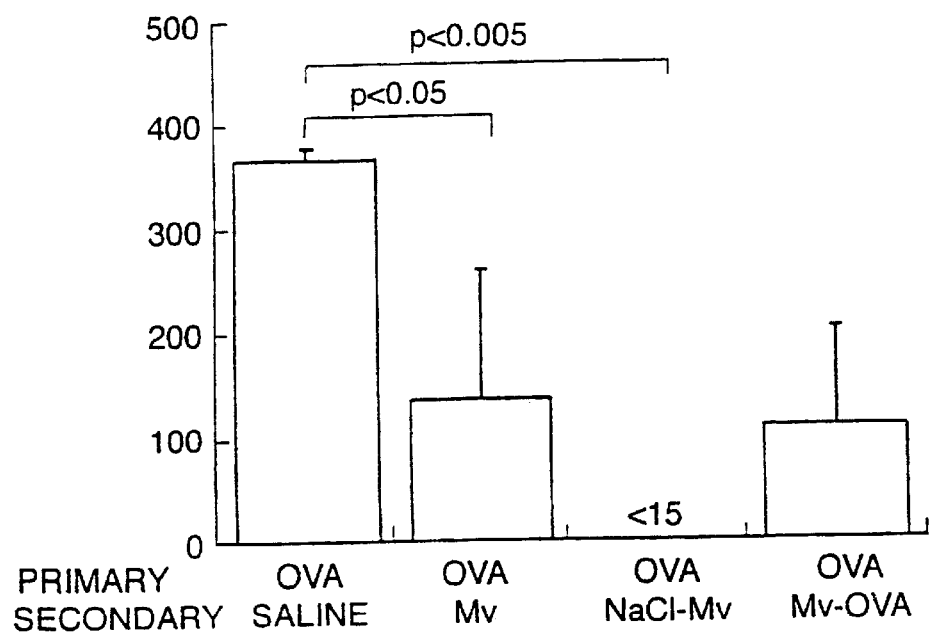

FIG. 6 shows production of IL-5 by splenocytes cultured with OVA. Spleens were obtained on day 109 from mice that had been immunized with OVA on days, 0 and 24, and treated on days 53 and 81 with saline, $10^7$ unmodified *M. vaccae* (Mv), OVA conjugated *M. vaccae* (Mv-OVA), or the corresponding control NaCl-washed and periodate-treated *M. vaccae* (NaCl-Mv). Culture supernatants were collected for IL-5 estimation after 48 hours. The data are presented as the mean levels of IL-5±SD (pg/ml).

Figure 7:
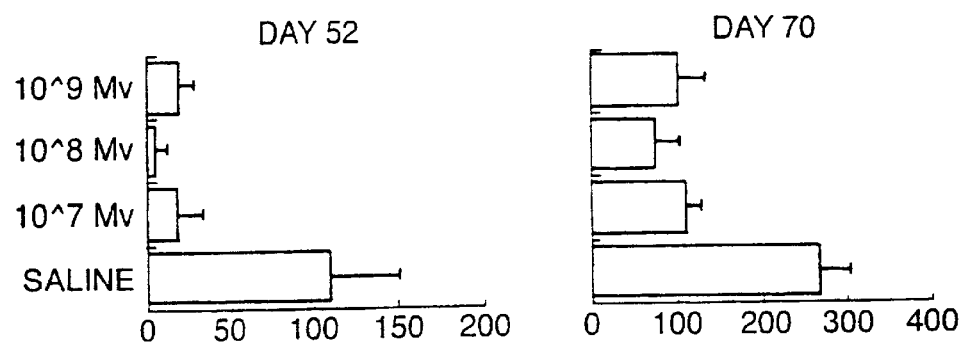

FIG. 7 shows the effect of treatment with single s.c. injections of different doses of *M. vaccae* compared to saline on serum IgE levels in BALB/c mice previously immunised with OVA. Serum IgE is expressed as the change (ng/ml) relative to readings obtained with the samples taken on day 32, before the treatment with *M. vaccae* or saline (mean±SE). Post-treatment serum samples were collected on days 52 and 70 (i.e. 10 days and 28 days after the treatment with saline or *M. vaccae* on day 42). Immunisation and treatment schedules are indicated in experimental methods. Comparison between different groups was performed by the Mann-Whitney U-test.

Figure 8A:
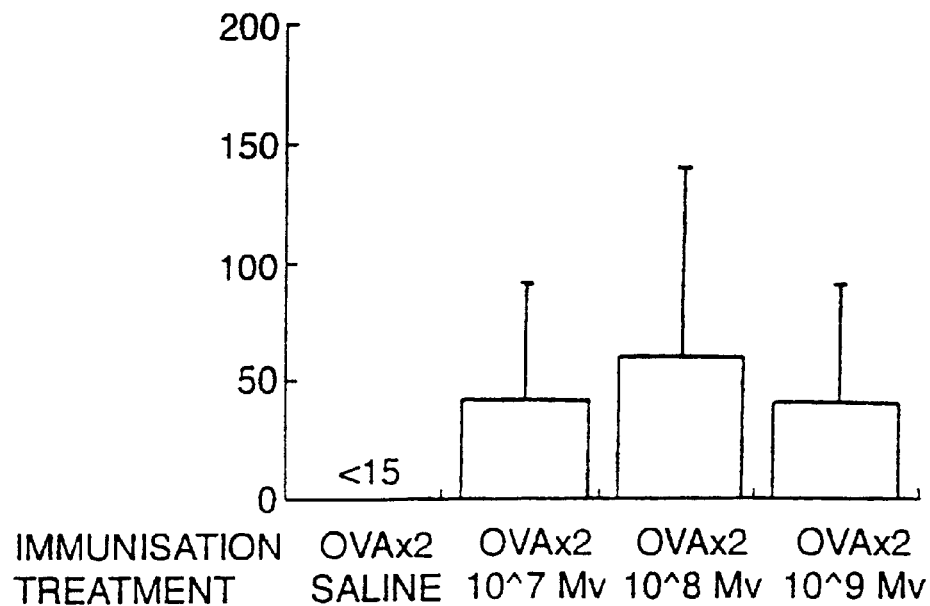
Figure 8B:
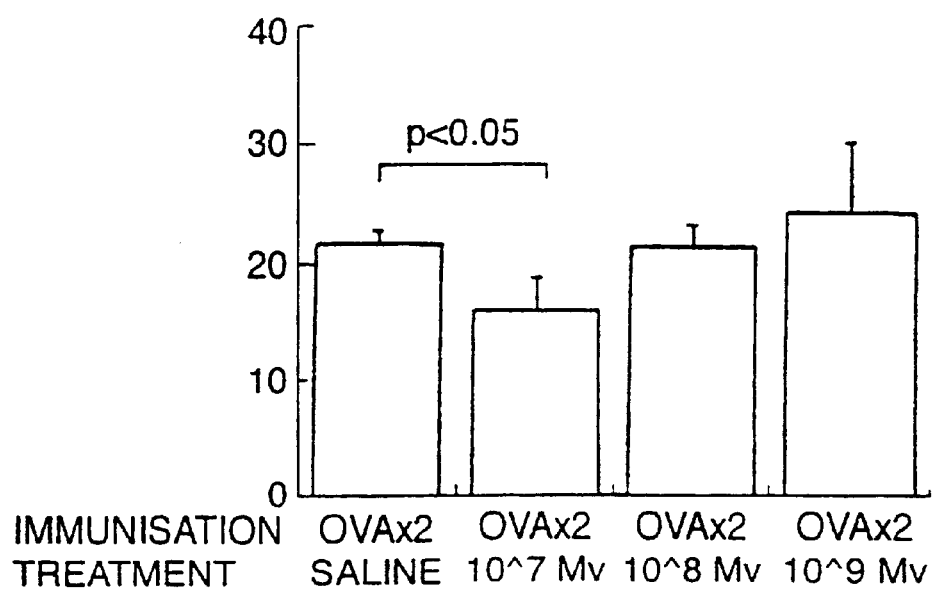

FIG. 8 shows production of IL-2 (FIG. 8A) and IL-4 (FIG. 8B) by splenocytes with OVA.BALB/c mice were given OVA twice prior to the different doses of *M. vaccae*:$10^7$, $10^8$, or $10^9$ (pg/ml). Splenocytes were harvested and cultured with OVA on day 82. Immunisation and treatment schedules are indicated in experimental methods. Culture supernatants were collected for IL-4 estimation after 48 hours and for IL-2 after 24 hours. The data are presented as the mean levels of cytokine±SD. Comparison between different groups was performed by Student's t-test. (saline:immunisation twice with OVA prior to saline treatment; 10^7 Nv:immunisation twice with OVA prior to $10^7$ *M. vaccae* treatment).

Figure 9:
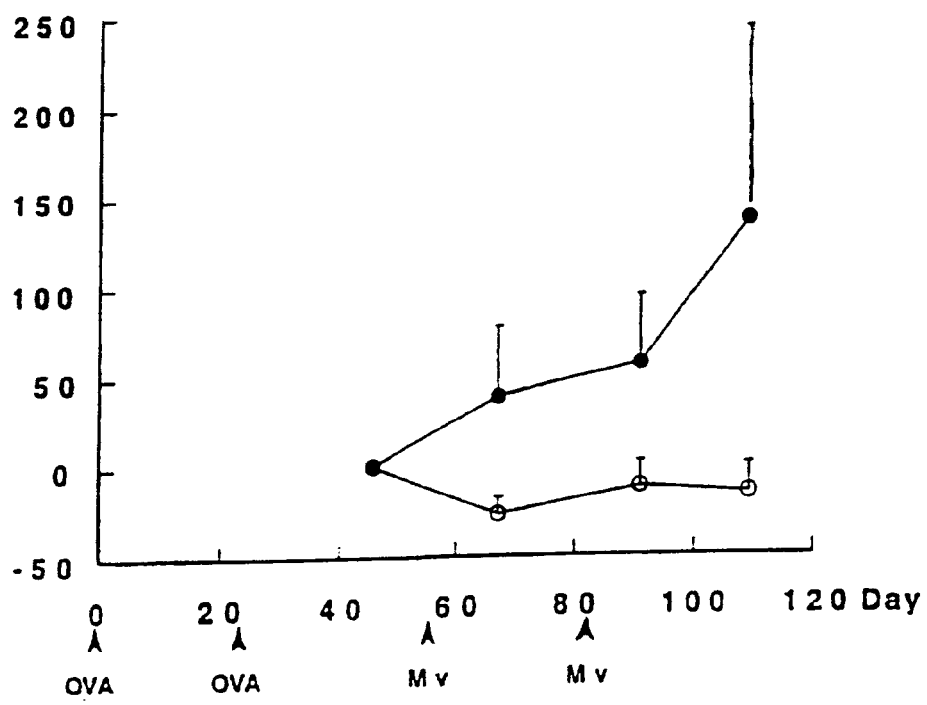
Figure 9:
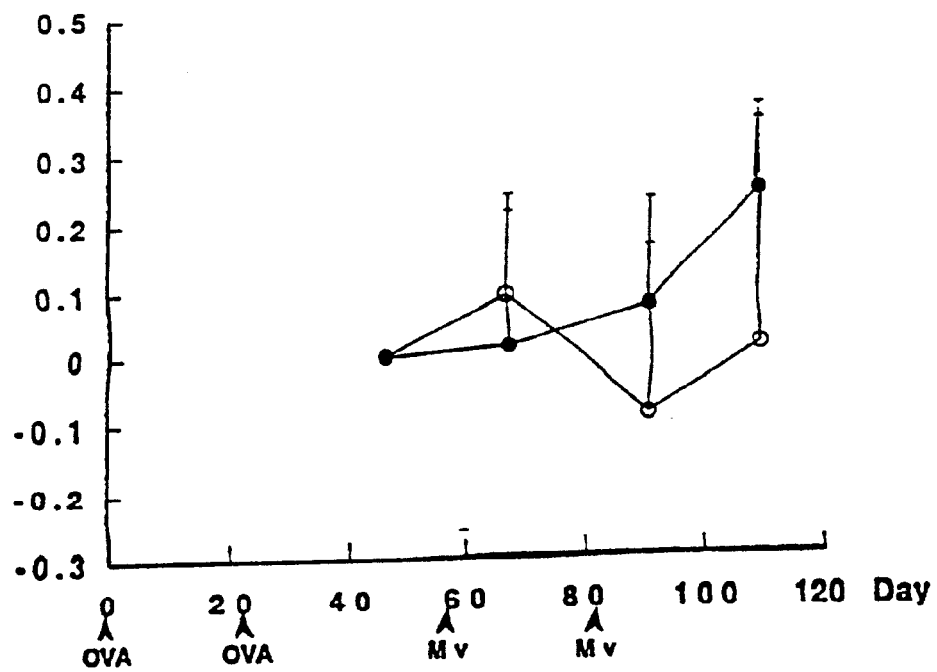

FIG. 9 shows the effect of treatment with two s.c. injections (days 53 and 81) of $10^7$ *M. vaccae* (O), compared to saline (•), on total serum IgE (FIG. 9A) and OVA-specific IgE (FIG. 9B). Immunisation and treatment schedules are indicated on the figure. Serum IgE is expressed as the change±SD relative to readings obtained with the samples taken on day 46 (ng/ml). Comparison between different groups was performed by the Mann-Whitney U-test. (OVA:ovalbumin immunisation;Mv:*M. vaccae* immunisation).

Figure 10A:
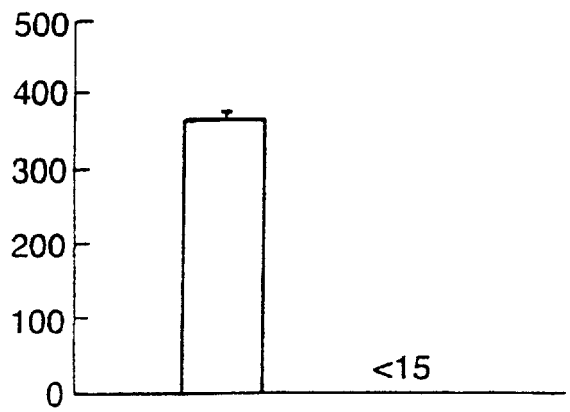
Figure 10B:
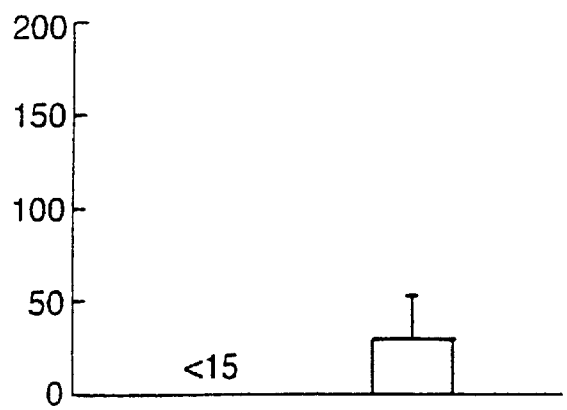
Figure 10C:
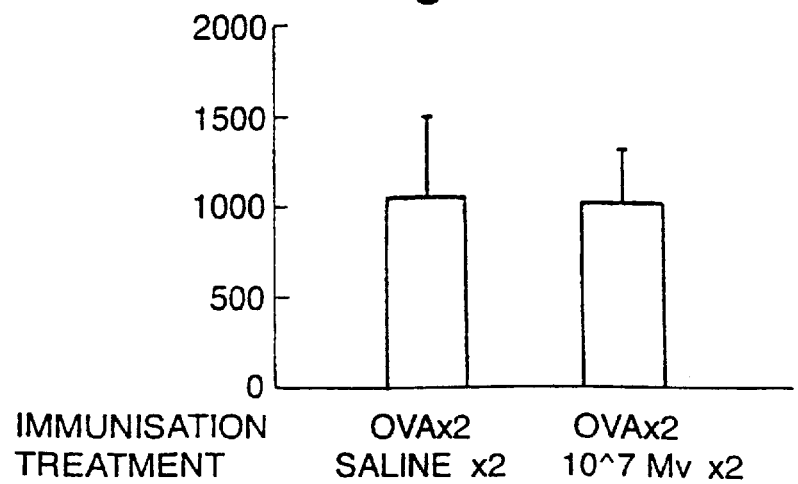

FIG. 10 shows production of IL-5 (FIG. 10A), IL-2 (FIG. 10B), and IFNγ (FIG. 10C) by splenocytes cultured with OVA (pg/ml). Splenocytes were harvested and cultured with OVA on day 109. Immunisation and treatment schedules are indicated on FIG. 9. Culture supernatants were collected for IL-5 estimation after 48 hours and for IFN-γ and IL-2 after 24 hours. The data are presented as the mean levels of cytokine±SD. Comparison between different groups was performed by Student's t-test. (saline:immunisation twice with OVA prior to saline treatment twice;$10^7$ Mv:immunisation twice with OVA prior to $10^7$ *M. vaccae* treatment twice).

All documents mentioned herein are incorporated by reference.

EXAMPLE 1

Administration of *M. vaccae* to Experimental Animals, and Demonstration of Resulting Non-specific Decrease in Th2 Activity of the Immune System Balb/c mice 6–8 weeks old were immunised with 50 µg ovalbumin emulsified in oil (incomplete Freund's adjuvant) on days 0 and 24. This is known to evoke a strong Th2 pattern of response, accompanied by IgE production, and priming for release of two Th2 cytokines, IL-4 and IL-5.

Animals then received saline or $10^7$ autoclaved *M. vaccae* on days 53 and 81 (by sub-cutaneous injection).

Serum samples were taken on days 46 (i.e. before treatment with saline or *M. vaccae*) and on days 67, 91 and 109.

Spleen cells were then harvested for challenge with ovalbumin in an in vitro culture system. Supernatants of the cultures were harvested at 48 hours for assay of cytokines by ELISA.

Capture assays were used, with antibody pairs from Pharmingen.

IL-5 #18051D capture; #18062D (biotinylated) detection. Binding of the detection antibody was revealed with streptavidin-horse radish peroxidase conjugate (Dako P0397) and the chromogen was ABTS (Sigma A-1888).

IgE #02111D capture; #02122D (biotinylated) detection. Binding of the detection antibody was revealed with avidin-alkaline phosphatase conjugate (Sigma E-2636) and the chromogen was pNPP (Sigma N-2770).

Results of IgE levels are expressed as the change in ng/ml compared to the serum concentration on day 46 (the last value before treatment). Thus the day 46 value is subtracted from the value in each subsequent bleed.

Results

Injections of *M. vaccae* reduced the rise in IgE levels caused by immunisation with ovalbumin. The reduction caused by treatment with *M. vaccae* was significant at all time points tested. The results are shown in FIG. 1.

Similarly, spleen cells from the immunised animals failed to release IL-5 in vitro in response to ovalbumin if the donor animals had been treated with *M. vaccae,* while spleen cells from immunised animals treated with saline released large quantities of IL-5 in response to ovalbumin. The results are shown in FIG. 2. No IL-5 was detected in control wells cultured without ovalbumin (data not shown).

Conclusion

*M. vaccae* will reduce a Th2 pattern of response, even when given:

(i) after immunisation with a potent allergen (in this case ovalbumin), and (ii) without epitopes of the Th2-inducing molecule.

There is therefore a non-specific systemic downregulation of the Th2 pattern of response, not dependent upon a direct adjuvant effect on the allergen itself.

EXAMPLE 2

The Effect of Different *M. vaccae* Preparations or Serum IgE

In a further experiment to determine the effect of conjugated *M. vaccae*-OVA on serum IgE titre, BALB/c mice were immunized with OVA in IFA twice to induce IgE responses, then treated twice with saline, unmodified *M. vaccae,* conjugated *M. vaccae*-OVA or the corresponding non-OVA-containing "mock"-conjugated preparation, NaCl-washed, periodate-treated *M. vaccae* (NaCl-Mv). On day 46 the OVA-immunized mice had 112.9±10 (S.E.) ng/ml IgE, compared to 55.4±1.7 (S.E.) ng/ml in unimmunized animals (p<0.01). For each mouse the day 46 value was used to normalise data to a starting (i.e. day 46) value of 0, and subtracted from each subsequent value. Therefore the values plotted are the changes in ng/ml relative to day 46.

The total serum IgE in control mice (treated with saline) increased steadily for the duration of the experiment (FIGS. 3A–C). There was suppression of total IgE in mice treated with unmodified *M. vaccae* (FIG. 3A). In contrast the NaCl-washed, periodate-treated preparations were not effective in IgE-suppression, whether conjugated to OVA (FIG. 3B) or unconjugated (FIG. 3C), although one dose of control NaCl-Mv showed a transient suppression of total serum IgE (p<0.05) (FIG. 3C). These results indicated that the ability to downregulate IgE was abrogated by the NaCl wash or by the conjugation procedure.

In contrast, neither unmodified *M. vaccae* nor the control NaCl-Mv downregulated OVA-specific IgE (FIGS. 4A and 4C). Moreover the OVA-specific IgE response was actually enhanced by treatment with conjugated Mv-OVA (FIG. 4B).

EXAMPLE 3

The Effect of Different *M. vaccae* Preparations on IL-2 Production by Spleen Cells Spleen cells from mice immunized with OVA were harvested on day 109, and cultured with OVA in vitro. Spleen cells from OVA-sensitized mice that received saline treatment failed to produce IL-2 in response to OVA in vitro. Spleen cells from immunized mice treated with the *M. vaccae* preparation that did not contain OVA components, produced detectable levels of IL-2 in response to OVA but the increase was not significant. In contrast, spleen cells from mice treated with the conjugated OVA-containing *M. vaccae* preparation released high levels of IL-2 in response to OVA (p<0.05 compared to saline recipients) (FIG. 5). These results revealed that conjugation of OVA on *M. vaccae* increased IL-2 production in response to OVA.

Thus, there is no significant increase in Th1 response to ovalbumin unless the ovalbumin is included (conjugated to) the *M. vaccae*. Moreover, as indicated, when ovalbumin is included, although the Th1 response then becomes highly significant, the suppression of Th2 is not improved, and may be decreased (see other experiments herein).

EXAMPLE 4

The Effect of Different *M. vaccae* Preparations on IL-5 Production by Spleen Cells Spleen cells from OVA-sensitised mice produced high levels of IL-5 in response to OVA (FIG. 6). However, cells from OVA-immunized mice that had been treated with *M. vaccae,* whether unmodified, NaCl-washed control, or OVA-conjugated, all released significantly less IL-5 in response to OVA. Thus in contrast to the results seen when IgE was measured, neither the conjugation procedure itself, nor the presence of OVA conjugated to the *M. vaccae,* had any effect on the downregulation of IL-5 release. If anything, the ability to switch off IL-5 was decreased by conjugation of the allergen onto the *M. vaccae,* since the relevant control for the Mv-OVA was the NaCl-Mv (mock conjugated).

EXAMPLE 5

The Effect of Different Doses of *M. vaccae* on Serum IgE in Animals

To determine the effect of different doses of *M. vaccae* on total serum IgE, BALB/c mice were immunized with OVA in IFA twice (day 0 and 21) to induce IgE responses. They were bled on day 32, and then treated with saline or with $10^7$, $10^8$, or $10^9$ *M. vaccae* on day 42.

On day 32 the OVA-immunized mice had 117.09±35.81 (S.D.) ng/ml IgE, compared to 69.27±6.09 (S.D.) ng/ml in unimmunized animals (p<0.001). For each mouse the day 32 value was used to normalise data to a starting (i.e. day 32) value of 0, and subtracted from each subsequent value. Therefore the values plotted are the changes in ng/ml relative to day 32.

The IgE response in control mice (treated with saline) had increased further by days 52 and 70 when further samples were taken (i.e. 10 and 28 days after treatment on day 42) (FIG. 7). In contrast, the increase in IgE level was suppressed in mice treated with *M. vaccae* at $10^7$, $10^8$, and $10^9$ (FIG. 7). All p values are less than 0.01 between mice treated with saline and different doses of *M. vaccae*.

EXAMPLE 6

The Effect of *M. vaccae* Treatment on Cytokines Production by Spleen Cells

BALB/c mice were subjected to the same protocol used for Example 5. Then on day 82, their spleen cells were harvested and cultured with OVA, *M. vaccae,* and ConA in vitro. Spleen cells from the saline treated group produced IL-4 but no IL-2, in response to OVA (FIGS. 8A/B). Splenic cells from OVA-immunized mice that had been treated with $10^7$ autoclaved *M. vaccae* showed IL-2 synthesis and decreased IL-4 production in response to OVA. IL-2 synthesis in response to OVA was also seen using spleen cells from mice treated with $10^8$ or $10^9$ M. vaccae.

Note that increase in IL-2 production in the M. vaccae-treated mice was not significant (the SD being greater than the responses), only involving some of the mice in the group. Most of the treated mice did not produce any IL-2.

EXAMPLE 7
The Effect of Two Doses of M. vaccae on Serum IgE

Since $10^7$ M. vaccae had been shown previously to be the optimal dose for evoking Th1 responses to its own antigens, and had been the most effective dose in the pilot experiments (FIG. 7), this dose was selected for further studies. BALB/c mice were immunized with OVA twice on day 0 and 24 to induce IgE responses and bled on day 46, and then treated with saline, or with $10^7$ M. vaccae twice on days 53 and 81. On day 46 the OVA-immunized mice had 112.9±10 (S.E.) ng/ml IgE, compared to 55.4±1.7 (S.E.) ng/ml in unimmunized animals ($p<0.01$). For each mouse the day 46 value was used to normalise data to a starting (i.e. day 46) value of 0, and subtracted from each subsequent value. Therefore the values plotted are the changes in ng/ml relative to day 46.

The total serum IgE response in control mice (treated with saline) increased steadily for the duration of the experiment. In contrast, the increase in IgE was suppressed in mice treated with $10^7$ autoclaved M. vaccae (FIG. 9A). Meanwhile, the suppression of anti-OVA IgE by the treatment of M. vaccae was not significant by this assay (FIG. 9B). However, further experiments show that OVA-sensitized BALB/c mice that received M. vaccae 4 times had significantly lower-OVA-specific IgE titers.

IgG1 and IgG2a antibodies to OVA were not affected by M. vaccae treatment.

EXAMPLE 8
The Effect of M. vaccae Treatment on IFN-$\gamma$, IL-2 and IL-5 Production by Spleen Cells BALB/c mice were subjected to the same protocol used for Example 7. Then on day 109, their spleen cells were harvested and cultured with OVA in vitro. Spleen cells from the saline treated group produced high levels of IL-5, but no IL-2, in response to OVA. However, cells from OVA-immunized mice that had been treated twice with $10^7$ autoclaved M. vaccae failed to release IL-5 in response to OVA (FIG. 10A). IL-4 production in response to OVA by spleen cells from mice that had received 2 doses of $10^7$ M. vaccae appeared to be reduced, but the levels of this cytokine were too close to the detection limit of the immunoassay to be reliable. As shown above (FIG. 8A), OVA induced IL-2 production was again detectable in supernatants from spleen cells of some mice treated with M. vaccae (FIG. 10B), though statistically insignificantly. Decreased Th2 was seen in animals that did not show increased IL-2. There was no difference in OVA-induced IFN-$\gamma$ synthesis by spleen cells from the different groups (FIG. 10C).

Discussion

BALB/c mice that received two immunizations with OVA in IFA developed a typical Th2 type response. There were rising levels of serum IgE, and spleen cells from these mice released IL-5 but not IL-2 in response to OVA in vitro. The most striking finding is that this ongoing allergen-specific response in BALB/c mice was downregulated by treatment with a low dose of killed M. vaccae without any need for OVA or OVA epitopes in the M. vaccae preparation.

Similarly our experiments revealed that high levels of serum IgE induced by OVA were suppressed by a wide range of doses of M. vaccae. This is unexpected because previous dose-response studies in mice identified $10^7$ as the optimum for inducing a Th1 response to the mycobacterial antigens contained within M. vaccae, with no detectable Th2 component, while $10^9$ evokes a mixed Th1+Th2 response. For all these reasons it is likely that the effects of M. vaccae in this model may not operate via the suppressive effects of Th1 cytokines. A further level of regulation of IgE levels may be attributable to the induction of IgE-binding factors.

There is no signficant increase in Th1 response to ovalbumin unless the ovalbumin is included (conjugated to) the M. vaccae, and when it is included, although the Th1 response becomes highly significant, the suppression of Th2 is not improved, and may be decreased.

EXAMPLE 9
Measurement of Th2 and Th1 Cytokine Profiles

There are some data on cytokine profiles in CFS and Gulf War Syndrome, but these are conflicting and use methods that are not reliable, though the overall clinical picture suggests an increased Th2/Th1 ratio as described above (Straus, 1996).

The optimal technology to demonstrate this is flow cytometry to enumerate precise numbers and percentages of T cells from the peripheral blood that are spontaneously secreting IL-2 (Th1) or IL-4 or IL-5 (both Th2), or that can be induced to secrete these cytokines after stimulation in vitro with calcium ionophore and phorbol myrystate acetate (PMA). (Secretion is in fact blocked by an inhibitor (monensin) so that the cytokine accumulates within the cell, where it is detected (after fixation and permeabilisation) with an appropriate fluorochrome-labelled monoclonal antibody.)

Using this technology, Th2 cells are extremely rare in the peripheral blood of normal donors, but can be common in the circulation of patients with chronic infection or cancer (unpublished observations).

A second technique is the direct measurement of cytokine levels in the plasma or serum. Interleukin 13 (IL-13) can be detected as a representative of the Th2 cytokines, and interferon gamma (IFN$\gamma$) as a representative Th1 cytokine.

The cytokine profiles of Gulf War veterans are examined using one of these techniques. Determination of a Th1$\rightarrow$Th2 bias is indicative of applicability of M. vaccae administration for amelioration of the symptoms.

EXAMPLE 10
Preparation of M. vaccae for Administration

M. vaccae is grown on a solid medium including modified Sauton's medium (Boyden et al.) solidified with 1.3% agar. The medium is inoculated with the microorganisms and incubated aerobically for 10 days at 32° C. to enable growth of the microorganism to take place. The microorganisms are then harvested and weighed and suspended in diluent to give 100 mg of microorganisms/ml of diluent. The suspension is then further diluted with buffered saline to give a suspension containing 10 mg wet weight (about $10^{10}$ cells) of microorganism/ml of diluent and dispensed into 5 ml multidose vials. The vials containing the live microorganisms are then autoclaved (115° C.–125° C.) for 10 minutes at 69 kPa to kill the microorganisms. The therapeutic agent thus produced is stored at 4° C. before use.

EXAMPLE 11
Use of M. vaccae in Treatment of a Disorder Characterised by Th1/Th2 Cytokine Shift 0.1 ml of the suspension prepared in accordance with Example 3, containing 1 mg wet weight (about $10^9$ cells) of M. vaccae, is shaken vigorously then immediately administered by intradermal injection over the left deltoid muscle.

Th1 and Th2 cytokine levels in the patient can be measured periodically to confirm shift from Th2 to Th1, particularly down-regulation of Th2 activity, while observing amelioration of the patient's symptoms.

EXAMPLE 12

Treatment of Patients with Chronic Fatigue Syndrome Using *M. vaccae*

(1) A patient aged 70 years being treated with SRL-172 for a squamous-cell lung cancer and with a coexisting diagnosis of Chronic Fatigue Syndrome, reported, with excitement, the lifting of her symptoms of the latter after 2 injections of SRL-172. She felt much better in herself and her "miseries had lifted". As an organ teacher, she has taken on several additional pupils—indicating her improvement. This patient has been treated with SRL172 for more than 1 year and reports continued well-being.

(2) A patient had a history of CFS for 7–8 years with symptoms which included general fatigue, migraines, depression, food allergies and lymphadenopathy. After 2 injections of SRL172 she reported improvement. Her sore throats and swollen glands and food allergies were much improved and she needed a smaller dose of Thyroxin. She spoke in a much brighter way and said she was less depressed.

(3) A patient's symptoms took the form of headaches, depression and multiple food allergies. Before treatment with SRL172 many other forms of treatment had been tried with no effect. In an attempt to control her symptoms large amounts of Nalcron were regularly taken (80 capsules of Nalcron 100 mg before and after one meal each day). Since she has been receiving SRL172 at 2-monthly intervals her symptoms of CFS, as well as her food allergy have considerably improved and she believes herself to be very well as long as she continues with her regular injections.

REFERENCES

Aaby, P. (1995) Soc. Sci. Med. 41: 673–86.
Aaby et al., (1995) Brit. Med. J. 311: 481–5.
Abou-Zeic et al., (1997) Infect. Immun. 65: 1856–1862.
Bernton et al., (1995) Ann. NY Acad. Sci. 774: 217–231.
Bonicke et al., (1964) Zentr albl. Bakteriol. Parasitenkd. Infection skr. Hyg. Abt. 1, Orig., 192: 133
Boyden et al., (1955) J. Immunol. 75: 15.
Bretscher et al., (1992) Science 257: 539–542.
Brinkmann et al., (1995) J. Immunol. 155: 3322–8.
Brown et al., (1993) Infect. Immun. 61: 4793–4800.
Casale et al., (1993) Immunopharmacol Immunotoxicol 15: 199–215.
Corrigan et al., (1995) Am. J. Respir. Cell. Mol. Biol. 12: 567–78.
Daynes et al., (1989) Eur. J. Immunol. 19: 2319–2325.
Daynes et al., (1990) J. Exp. Med. 171: 979–996.
Daynes et al., (1993) J. Immunol. 150: 5219–5230.
Daynes et al., (1995) J. Invest. Dermatol. 105: 14S–19S.
Daynes et al., (1991) Res. Immunol. 142: 40–45.
Fischer et al., (1991) Immunology 74: 228–233.
Fukuda et al., (1994) Ann. Int. Med 121: 953–9
Garg et al., (1993) Infect. Immun. 61: 2238–2241.
Glaser et al., (1993) Behav. Neurosci. 107: 525–9.
Guida et al., (1994) Blood 84: 2733–40.
Hernandez-Pando et al., (1994) Immunology 82: 591–595.
Holsboer et al., (1984) New Eng. J. Med. 311: 1127–.
Morales et al., (1994) J. Clin. Endocrinol. Metab. 78: 1360–1367.
Moynihan, J. (1994) Advances: Mind Body Health 10: 23–28.
Mu et al., (1993) Infect. Immun. 61: 2834–2840.
Nilsson et al., (1996) JAMA 275: 760.
Odent et al., (1994) JAMA 272: 592–593.
Padgett et al., Ann. NY Acad. Sci. 774: 323–325.
Ramirez et al., (1996) J. Immunol. 156: 2406–2412.
Ramiya et al., (1996) J. Autoimmun. 9: 349–356.
Raven et al., (1995) Clin. Endocrinol. 43: 637–644.
Raven et al., (1996) Psychoneuroendocrinology 21: 277–286.
Rook et al., (1996) Annu. Rev. Microbiol. 50: 259–284.
Rook et al., (1996) Q. J. Med. 89: 333–341.
Rupprecht et al., (1995) Psychoneuroendocrinology 20: 543–551.
Shaheen et al., (1996) Lancet 347: 1792–6.
Skinner et al., (1997a) *Vaccines beyond Jul.* 6–9, 2000, *Queensland Australia, Abstract*
Skinner et al., (1997b) *Infect. Immun.,* 65: 4525–4530.
Stanford and Paul, (1973) Ann. Soc. Belge Med. Trop. 53: 141–389.
Sharp et al., (1991) J. R. Soc. Med. 84: 118–21.
Shirakawa et al., (1996) Science In press.
Smit et al., (1996) Transplant Proc. 28: 665–666.
Straus, S (1996) NIH Publication No. 90-3059: 1–5.
Suzuki et al., (1991) Clin. Immunol. Immunopathol. 61: 202–211.
Tobach et al., (1956) Am. J. Physiol. 187: 399–402.
Turnberg et al., (1996) Report of a joint working group of the Royal Colleges of Physicians, Psychiatrists and General Practitioners. London: Royal College of Physicians 58: vol. 1).
Wu et al., (1991) J. Clin. Invest. 87: 870–877.
Zwilling, B. S. (1992) ASM News 58: 23–25.

What is claimed is:

1. A method of treating a disorder characterised by an up-regulation of Th2 activity of the immune system of an individual comprising;

determining the amount of Th2 activity in the immune system of an individual; and, administering to the individual an amount of a composition comprising antigenic and/or immunoregulatory material of *Mycobacterium vaccae* and not any non-*M. vaccae* antigen, immunogen or allergen, sufficient to reduce Th2 activity of said immune system without increasing the Th1 activity thereof.

2. A method according to claim 1 wherein the antigenic and/or immunoregulatory material of *M. vaccae* comprises dead cells of *M. vaccae*.

3. A method according to claim 2 wherein the cells have been killed by autoclaving.

4. A method according to claim 1 wherein the disorder is Chronic Fatigue Syndrome.

* * * * *